US007613500B2

(12) United States Patent
Vass et al.

(10) Patent No.: US 7,613,500 B2
(45) Date of Patent: *Nov. 3, 2009

(54) METHODS AND APPARATUS FOR ASSISTING CARDIAC RESYNCHRONIZATION THERAPY

(75) Inventors: Melissa L. Vass, Milwaukee, WI (US); Darin R. Okerlund, Muskego, WI (US); Laurent Launay, Saint Remy les Chevreuse (FR); Jasbir Singh Sra, Pewaukee, WI (US)

(73) Assignee: General Electric Company, Schenectady, NY (US)

(*) Notice: Subject to any disclaimer, the term of this patent is extended or adjusted under 35 U.S.C. 154(b) by 662 days.

This patent is subject to a terminal disclaimer.

(21) Appl. No.: 10/900,847

(22) Filed: Jul. 28, 2004

(65) Prior Publication Data

US 2005/0096523 A1    May 5, 2005

Related U.S. Application Data

(63) Continuation-in-part of application No. 10/605,903, filed on Nov. 5, 2003, now Pat. No. 7,308,297.

(51) Int. Cl.
*A61B 5/05* (2006.01)
(52) U.S. Cl. .................. 600/427; 600/411; 600/425; 382/131
(58) Field of Classification Search ................ 600/416, 600/425; 382/131; 378/21; 607/115, 116, 607/119, 122
See application file for complete search history.

(56) References Cited

U.S. PATENT DOCUMENTS 5,151,856 A * 9/1992 Halmann et al. ............ 600/508

| 6,424,731 | B1 | 7/2002 | Launay et al. |
| 6,510,241 | B1 | 1/2003 | Vaillant et al. |
| 6,526,117 | B1 | 2/2003 | Okerlund et al. |
| 6,628,743 | B1 * | 9/2003 | Drummond et al. ............ 378/8 |

(Continued)

FOREIGN PATENT DOCUMENTS

EP    1063617 A1    12/2000

(Continued)

OTHER PUBLICATIONS

Mor-Avi et al. Segmental Analysis of Color Kinesis Images. Circulation. 95: pp. 2082-2097. 1997.*

(Continued)

*Primary Examiner*—Brian Casler
*Assistant Examiner*—Parikha S Mehta
(74) *Attorney, Agent, or Firm*—Armstrong Teasdale LLP

(57) ABSTRACT

A method for assisting the planning of an interventional biventricular pacing procedure includes segmenting an image dataset of a heart of a patient to extract a surface of a left ventricle (LV) and a LV myocardium of the patient's heart, utilizing the segmented image dataset to divide the LV into myocardial segments or into a plurality of short axis slices, and detecting wall motion of each short axis slice of phases of a cardiac cycle of the patient's heart with respect to a reference phase. The method also includes localizing a region most recently attaining maximum displacement and a region most recently attaining maximum velocity, and generating 2D or 3D renderings including renderings indicating at least one of time delays of contraction, a maximum displacement, or a maximum velocity.

52 Claims, 7 Drawing Sheets

U.S. PATENT DOCUMENTS

| | | |
|---|---|---|
| 6,628,981 B2 | 9/2003 | Baker et al. |
| 2003/0187362 A1* | 10/2003 | Murphy et al. ............... 600/508 |
| 2004/0097805 A1 | 5/2004 | Verard et al. |
| 2004/0097806 A1 | 5/2004 | Hunter et al. |
| 2004/0098075 A1 | 5/2004 | Lee |

FOREIGN PATENT DOCUMENTS

| | | |
|---|---|---|
| EP | 1387320 A2 | 2/2004 |
| EP | 1394747 A1 | 3/2004 |
| WO | WO 02/056935 A2 | 7/2002 |
| WO | WO 02/064205 A2 | 8/2002 |

OTHER PUBLICATIONS

Park et al (Visualization and Analysis of Left Ventricular Wall Motion. Proceedings of the First Joint BMES/EMBS Conference. p. 186. Oct. 1999.).*

Mitchell et al (Multistage Hybrid Active Appearance Model Matching: Segmentation of Left and Right Ventricle in Cardiac MR Images. IEEE Transactions on Medical Imaging. 20(5): pp. 415-423. 2001).*

* cited by examiner

METHODS AND APPARATUS FOR ASSISTING CARDIAC RESYNCHRONIZATION THERAPY

CROSS REFERENCE TO RELATED APPLICATIONS

This application is a continuation in part of U.S. patent application Ser. No. 10/605,903 entitled "Cardiac imaging system and method for quantification of desynchrony of ventricles for beventricular pacing," filed Nov. 5, 2003, now U.S. Pat. No. 7,308,297 which is hereby incorporated by reference in its entirety.

BACKGROUND OF THE INVENTION

This invention relates generally to methods and apparatus for biventricular pacing planning, and more particularly to methods and apparatus for enabling an eletrophysiologist, cardiologist, and/or surgeon in planning an interventional approach to take for lead placement in biventricular pacing.

It is estimated that 6-7 million people in the United States and Europe alone have congestive heart failure (CHF), the most common causes of which are ischemic and idiopathic cardiomyopathies. Prolonged PR intervals and wide QRS complexes are present in 20-50% of patients with CHF. About 29% of these patients have left bundle branch block (LBBB).

Normal electrical conduction in the heart starts in the sinoatrial node and proceeds via the atrioventricular node, His bundle, and right and left bundle branches. In patients with CHF and LBBB, long mechanical delay is present, resulting in delayed ventricular depolarization that leads to delayed left ventricular ejection. In the presence of LBBB, contraction is asymmetrical. The septum shortens first followed by stretching of the lateral wall. Subsequently, the lateral wall shortens and the septum stretches, causing ineffective contraction of the left ventricle. Cardiac resynchronization therapy, in which both the right ventricle (RV) and the left ventricle (LV) are paced simultaneously, has been shown to be effective in improving function in patients with CHF and LBBB.

Recently it has been shown that biventricular dysynchrony can also be seen in some patients with normal QRS or right bundle branch block and that biventricular pacing may be helpful in these patients. Beneficial effects of biventricular pacing have also been demonstrated in patients with atrial fibrillation.

One known method for performing biventricular pacing includes positioning the RV and right atrial lead, followed by positioning a sheath in the coronary sinus (CS). An angiogram is then performed to delineate a suitable branch for LV lead placement. The lead for LV pacing is placed in the posterior or posterolateral branch of the CS, and both RV and LV leads are then used to pace the RV and the LV simultaneously, thereby achieving synchronization with atrial contraction.

In over 20% of patients for whom biventricular pacing might otherwise be helpful, lead placement in the CS may be an unsuccessful or very lengthy procedure or the lead may dislodge from the CS. Other difficulties that can occur that may inhibit the usefulness of the procedures include unavailability of a suitable CS branch, significant rotation of the CS due to left atrial (LA) and LV dilatation, and presence of the tebesian valve. In most instances, these problems can be identified only at the time of the interventional procedure, and the procedure is either abandoned or the patient is brought back to the operating room for a second procedure where, using a surgical incision, the LV lead is placed epicardially from outside.

Some of the pitfalls involved in the use of at least one known epicardial lead placement method include having a limited view of the posterolateral or lateral area of the LV using minithoracotomy. Also, the available placement may be limited to sites that provide reasonable pacing and sensing parameters. In some cases, there may exist an inability to determine how far the LV is from the thoracic wall and/or an inability to identify the posterolateral or lateral area of the left ventricle that contracts last during the heart cycle. The methods may also run a risk of damaging the coronary arteries and venous system. In some procedures, there is an increased level of difficulty due to the presence of extrapericardial fat or no visualization of normal versus scarred tissue due to limited visibility. There may also be a difficulty in identifying the ideal position for pacing due to all of the above limitations. Furthermore, although many techniques such as tissue Doppler studies and echocardiography have been used to identify left and right ventricular asynchrony, it is not possible to identify the location that may give the most benefit from resynchronization.

BRIEF DESCRIPTION OF THE INVENTION

Some aspects of the present invention therefore provide a method for assisting the planning of an interventional biventricular pacing procedure. The method includes acquiring a volume of data of a heart of a patient in diastolic phase and in a plurality of phases of systole and early diastole, wherein the acquired volume of data becomes an image dataset. The image dataset is segmented to extract a surface of the left ventricle (LV) and the LV myocardium. The method further utilizes the segmented image dataset to divide the LV into myocardial segments or into a plurality of short axis slices. The method further includes detecting wall motion of each short axis slice between phases of the cardiac cycle with respect to a reference phase, localizing a region most recently attaining maximum displacement and a region most recently attaining maximum velocity, and generating 2D or 3D renderings including renderings indicating at least one of time delays of contraction, a maximum displacement or a maximum velocity.

In other aspects, the present invention provides a system for assisting the planning of an interventional biventricular pacing procedure for a heart of a patient. The system includes an imaging apparatus configured to acquire a volume of data of a heart of a patient in diastolic phase and in a plurality of phases of systole and early diastole, wherein the acquired volume of data becomes an image dataset. The system is configured to segment the image dataset to extract a surface of the left ventricle (LV) and the LV myocardium, utilize the segmented image dataset to divide the LV into myocardial segments or into a plurality of short axis slices, and detect wall motion of each short axis slice between phases of the cardiac cycle with respect to a reference phase. The system is further configured to localize at least one of a region indicating time delays of contraction, a region most recently attaining maximum displacement, or a region most recently attaining maximum velocity, and generate 2D or 3D renderings including renderings indicating at least one of time delays of contraction, a maximum displacement, or maximum velocity.

In yet other aspects, the present invention provides a method for assisting the planning of an interventional biventricular pacing procedure. The method includes segmenting an image dataset of a heart of a patient to extract a surface of a left ventricle (LV) and a LV myocardium of the patient's heart, utilizing the segmented image dataset to divide the LV into myocardial segments or into a plurality of short axis slices, and detecting wall motion of each short axis slice of phases of a cardiac cycle of the patient's heart with respect to a reference phase. The method also includes localizing a region most recently attaining maximum displacement and a region most recently attaining maximum velocity, and generating 2D or 3D renderings including renderings indicating at least one of time delays of contraction, a maximum displacement, or a maximum velocity.

In still other aspects, the present invention provides a machine readable medium having recorded thereon instructions configured to instruct a processor to segment an image dataset of a heart of a patient to extract a surface of a left ventricle (LV) and a LV myocardium of the patient's heart. The instructions are also configured to instruct a processor to utilize the segmented image dataset to divide the LV into myocardial segments or into a plurality of short axis slices, detect wall motion of each short axis slice between phases of a cardiac cycle of the patient's heart with respect to a reference phase, localize a region most recently attaining maximum displacement and a region most recently attaining maximum velocity and, generate 2D or 3D renderings including renderings indicating at least one of time delays of contraction, a maximum displacement, or a maximum velocity.

In still other aspects, the present invention provides a computer system for assisting the planning of an interventional biventricular pacing procedure for a heart of a patient. The computer system has a processor, memory, and a display. The computer system is configured to segment an image dataset of the heart of the patient to extract a surface of the left ventricle (LV) and the LV myocardium of the patient's heart, utilize the segmented image dataset to divide the LV into myocardial segments or into a plurality of short axis slices, and detect wall motion of each short axis slice between phases of a cardiac cycle of the patient's heart with respect to a reference phase. The computer system is further configured to localize a region most recently attaining maximum displacement and a region most recently attaining maximum velocity, and generate 2D or 3D renderings including renderings indicating at least one of time delays of contraction, a maximum displacement, or a maximum velocity.

Configurations of the present invention can advantageously be used in planning to view distances from chest wall to heart surface, to identify locations for incision, and to facilitate surgical planning by viewing anatomical structures and their orientation in a patient before surgery. Configurations of the present invention can also be used to view the CS and CS orientation as well as a location of a closest branch to an optimal or at least advantageous site, thereby providing information to help determine a strategy as to how a lead can be navigated using a transvenous approach, wherein an LV lead is placed in a branch of the CS.

It will further be appreciated that configurations of the present invention can be used to navigate the pacing lead in real time to a location that achieves the most coordinated ventricular contraction, or can be used in other than real time for planning purposes. Moreover, configurations of the present invention can play a significant role in providing LV anatomy and function and thus identify the most appropriate location for lead placement, thereby providing reduced overall procedure time and increased efficacy and safety.

DETAILED DESCRIPTION OF THE INVENTION

Figure 1:
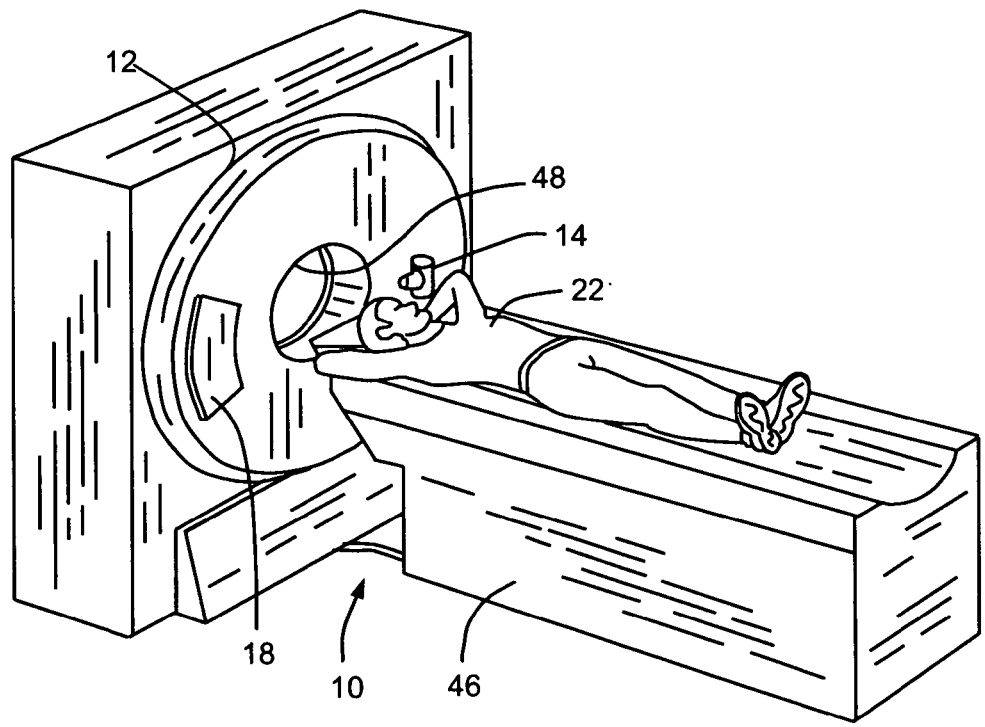
FIG. 1 is a perspective pictorial view of a configuration of a computed tomographic (CT) imaging system.

The present invention, in some aspects, provides a cardiac CT system and method for biventricular pacing planning. Technical effects of the systems and methods disclosed herein include providing information and images for planning interventional procedures, thereby enabling a electrophysiologist, cardiologist, and/or surgeon to plan in advance an approach to take for the procedure. Other technical effects include providing a detailed 3D geometrical representation of the LV and its relationship to the thoracic wall, so that a electrophysiologist, cardiologist, and/or surgeon can the presence of fat, the location and orientation of the major blood vessels and their branches and viable tissue which can be used for placement of the LV lead. A technical effect of some configurations includes providing visualizations to identify the best location for placement of LV pacing lead. Similarly, if a transvenous approach is used, some configurations include identification and visualization of an optimal or at least an advantageous CS branch for lead placement.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
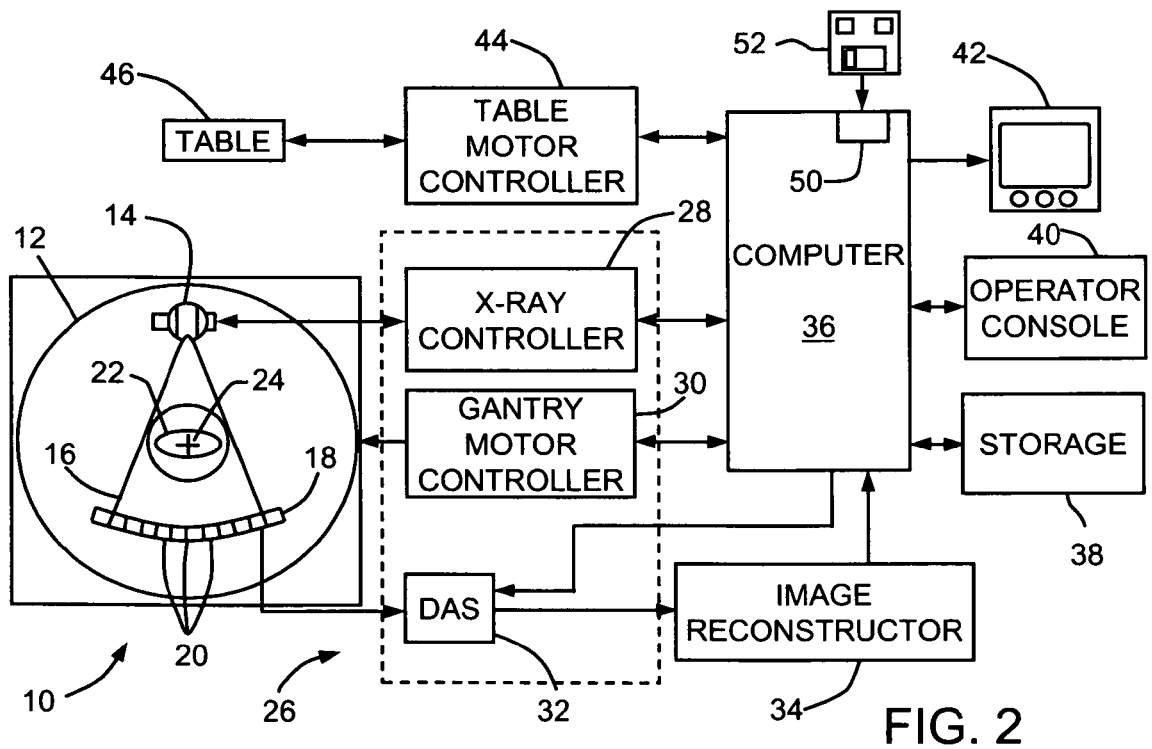
FIG. 2 is a functional block diagram of the configuration of CT imaging system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36. Computer 36 includes a processor that can execute machine readable instructions from a media source and/or memory and/or a wired or wireless network.

Computer 36 also receives commands and scanning parameters from an operator via console 40 that has a keyboard. An associated cathode ray tube display 42 (or other suitable display) allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in formware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. For example, some configurations of the present invention utilize magnetic resonance imaging (MRI) apparatus and datasets rather than x-ray CT imaging systems and datasets. Still other configurations of the present invention utilize ultrasound imaging apparatus and datasets in place of CT imaging systems and datasets. Still other configurations utilize 3D fluoroscopy imaging systems and datasets rather than CT imaging systems and datasets.

In some configurations of the present invention, a cardiac CT system for biventricular pacing planning provides information for planning interventional procedures, thereby enabling a electrophysiologist, cardiologist, and/or surgeon to plan in advance an approach to take for the procedure. In addition, a more detailed 3D geometrical representation of the LV and its relationship to the thoracic wall is provided. The electrophysiologist, cardiologist, and/or surgeon can use this more detailed representation to identify the presence of fat, the location and orientation of the major blood vessels and their branches and viable tissue which can be used for placement of the LV lead. Also, LV contractility can be visualized to identify the best location for placement of LV pacing lead. The information obtained from the cardiac CT system thus eliminates the need to place the lead blindly, while allowing for direct pacing lead placement via a surgical incision or endoscopic approach at the most beneficial location, which can be planned in advance. In addition, the pacing lead can be registered with an interventional system or fluoroscopy to enable precise placement of the lead.

Figure 3:
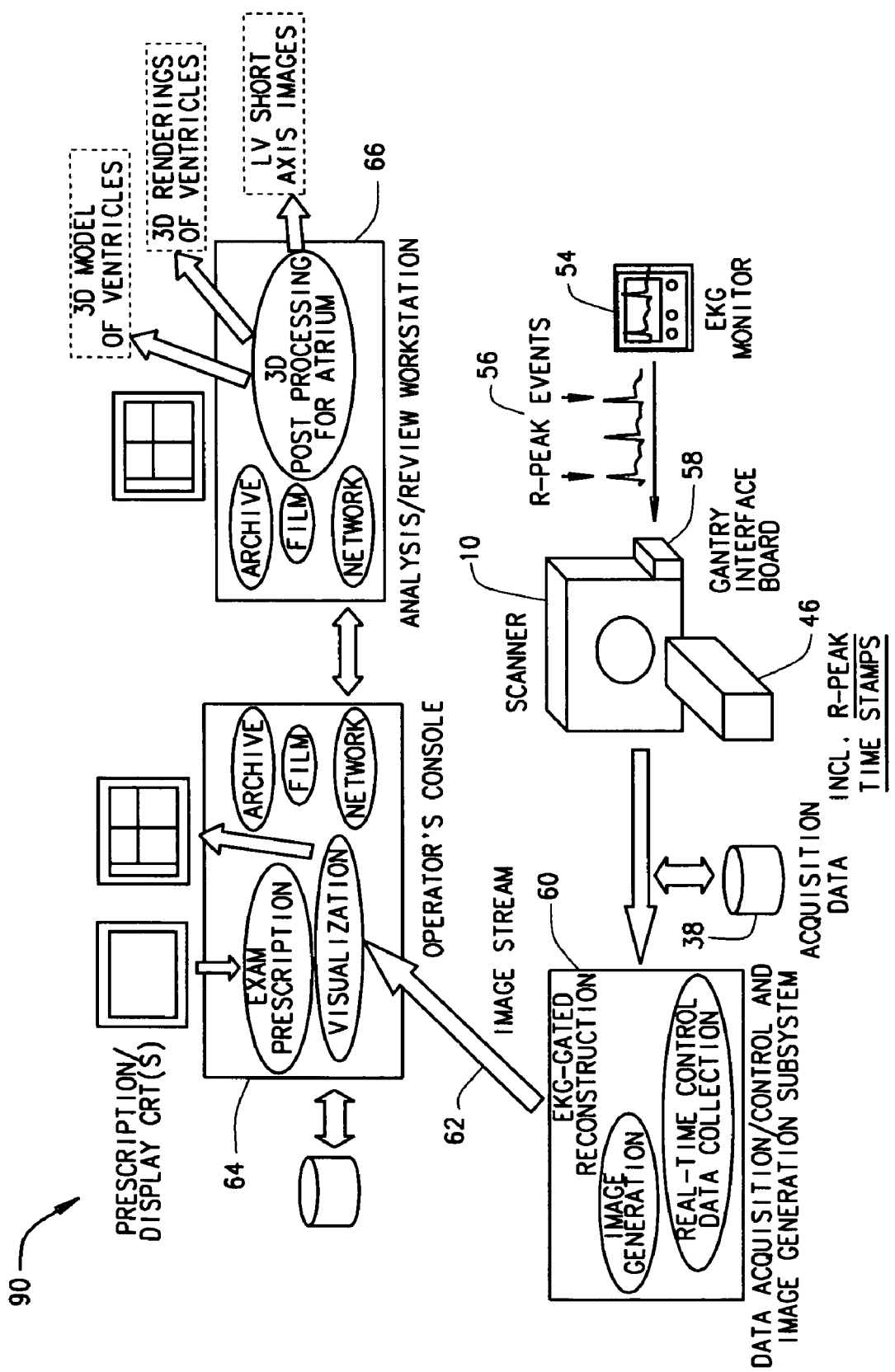
FIG. 3 is a functional block diagram of a configuration of a cardiac CT system that incorporates or uses the CT imaging system configuration illustrated in Figure and FIG. 2.

In some configurations and referring to FIG. 3, a cardiac CT system 90 for biventricular pacing planning for pacing lead placement includes a CT system 10 having EKG-gated acquisition and image reconstruction capabilities that is configured to image the heart of a patient 22 free of motion artifacts in diastolic phase of the cardiac cycle and also image the heart in multiple phases of systole and early diastole. The cardiac CT system includes one or more acquisition protocols that are optimized for or at least capable of imaging the heart, specifically the LV in diastole and multiple phases in systole and early diastole. An EKG monitor 54 monitors electrical signals from the heart of patient 22, for example, R-peak events 56. These signals are provided to a gantry interface board 58 that integrates data from the scanning of patient 22 with information relating to the cardiac cycle of patient 22. Acquired volumes of data (i.e., image datasets) in diastolic phase and in a plurality of phases of systole and early diastole can be stored in storage device 38 (part of CT system 10) or on media separate from CT system 10. This data is processed (either in real time or after storage and retrieval from device 38) at 60 using any suitable EKG-gated reconstruction technique to form an image dataset or stream 62. This data can be visualized (i.e., displayed) on an operator console or workstation 64 and further processed on an analysis/review workstation 66. Components of subsystems 60, 64, and 66 can be implemented as added functionality (e.g., programming) of components of CT imaging system 10 itself or as one or more separate workstations. For example, in some configurations, image reconstructor 34, computer 36, storage device 38, and display 42 are used to perform the functions of subsystems 60, 64, and 66 under appropriate software of formware control.

Thus, some configurations of the present invention provide cardiac post-processing software. This software includes one or more 3D protocols and short axis protocols from an automated image segmentation of the CT image dataset. The protocols include protocols for the LV anatomy, movement of LV walls during systole (LV contractility), epicardial fat location, location of viable tissue, and blood vessels and their branches and orientation. In some configurations the protocols provided include optimized 3D protocols.

Also included in some configurations is post-processing software that provides views of the LV and blood vessels and branches and slow motion cine of the LV, particularly the posterolateral and lateral wall of LV. These special views and video (cine) clips can be saved and viewed by the electrophysiologist, cardiologist, and/or surgeon.

Figure 4A:
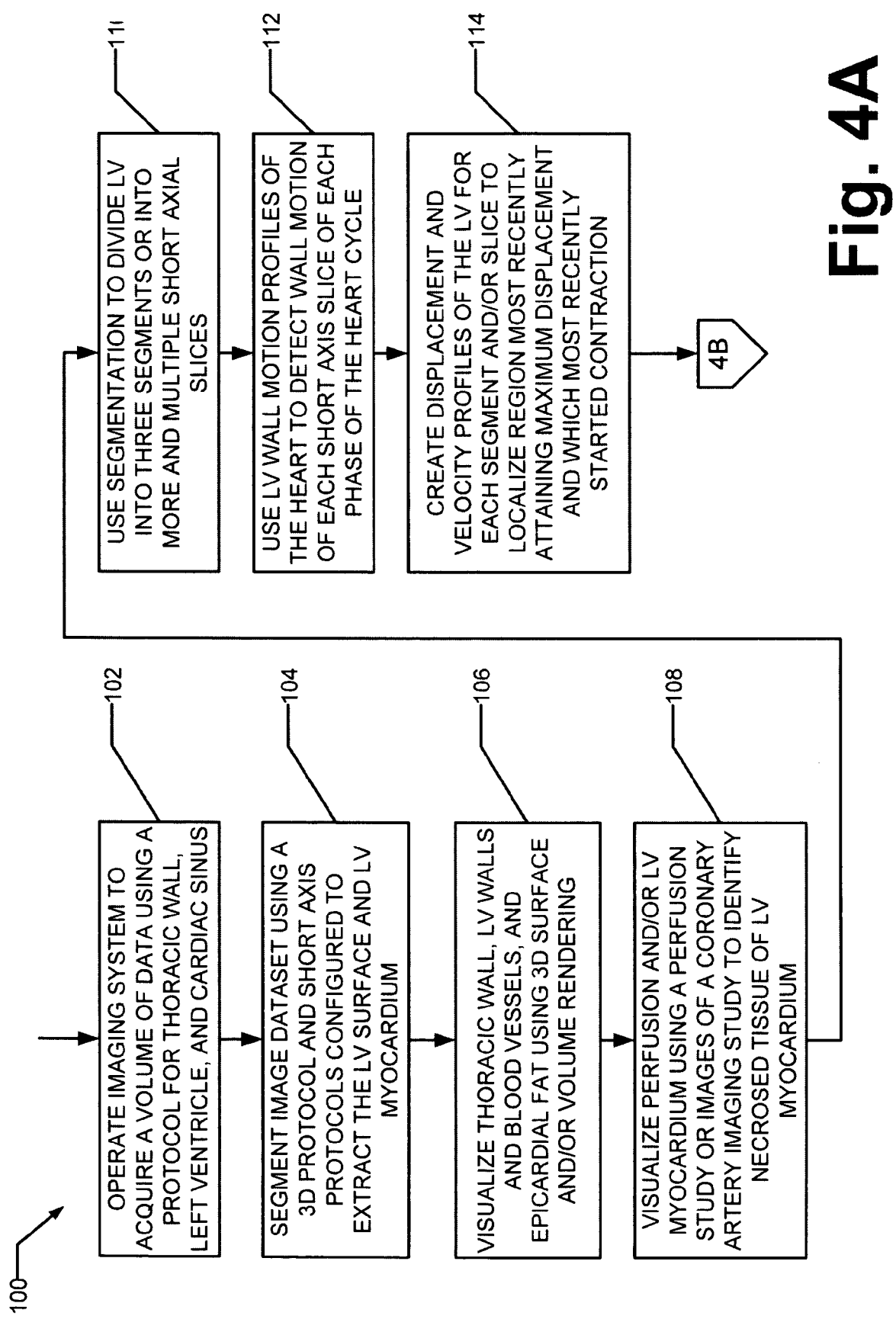
FIG. 4 is a flow chart representative of steps performed in some configurations of the present invention.
Figure 4B:
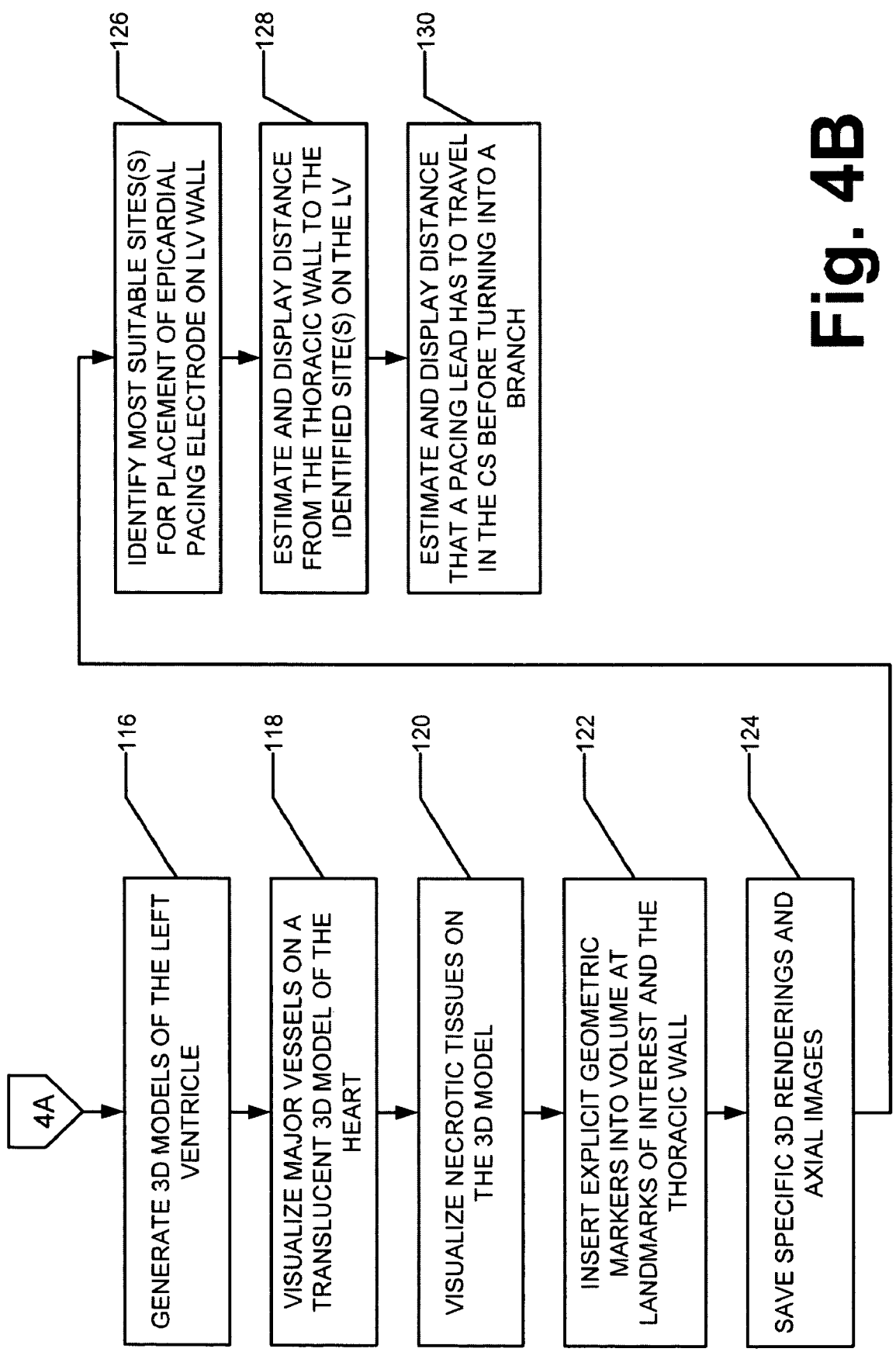
Figure 5:
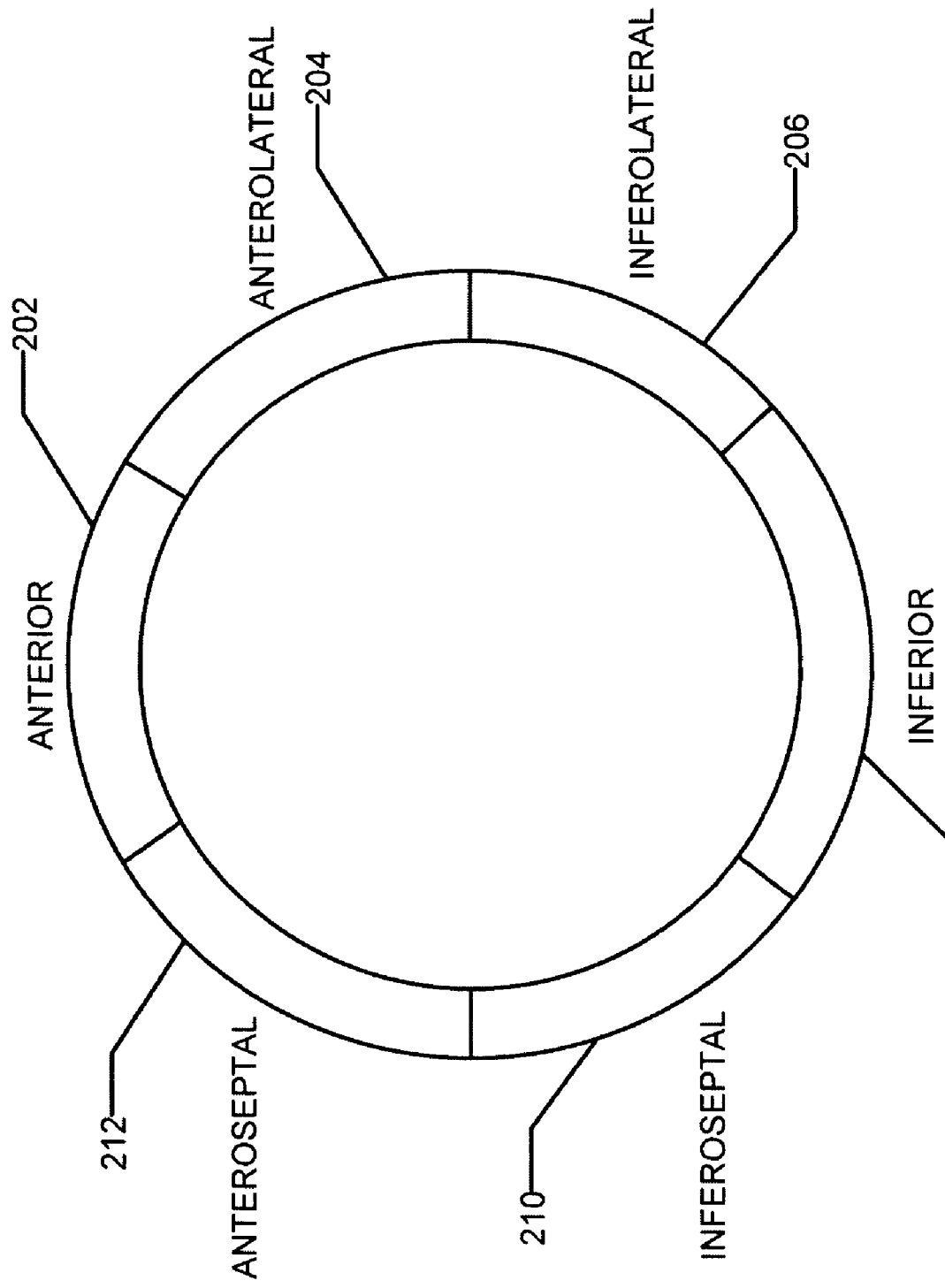
FIG. 5 is an illustration of the division of a short axis slice of a heart into six regions.

In some configurations and referring to flow chart 100 of FIG. 4, a technical effect of the present invention is achieved by a user first operating CT system 10 at 102 to acquire a volume of data using a protocol for the thoracic wall and LV and the CS, for example, a protocol optimized for such use. Under control of post-processing software, the image dataset is segmented at 104 using a 3D protocol and short axis protocols configured to identify and extract the surface of the LV and the LV myocardium. The automated procedures can be used where appropriate with or without queues from the operator e.g., location of anteroposterior, left anterior oblique, posterolateral, oblique and right anterior oblique views. Next, the thoracic wall, LV walls and blood vessels, and epicardial fat are visualized at 106 using 3D surface and/or volume rendering. (In some configurations, this visualization is performed using an image dataset that is a whole dataset [not a 3D rendering], because visualizing the path and measuring the chosen path and skin to heart distance used for surgical planning can be done from an axial, sagittal coronal, or oblique plane of the full volume as well as from a 3D rendering.) In some configurations, measurements indicating distances from skin to heart wall are also provided. Also in some configurations, the perfusion and/or viability of the myocardium of LV is visualized at 108 with a perfusion study or with images of the coronary artery imaging study to identify and to determine anatomical locations of any identified necrosed tissue of the LV myocardium. The segmentation is used at 110 to divide the LV into 3 myocardial segments (basal, said and apical) or into more and multiple short axis slices. The short axis slice of the myocardial wall is divided into a number of chords and bins, for example, 100 or more total chords and bins. Sixteen to seventeen chords are then used to create each of 6 or more regions. For example, and referring to FIG. 5, the short axis of the heart is divided into an anterior region 202, an anterolateral region 204, a posterolateral region 206, a posterior region 208, a posteroseptal region 210, and an anteroseptal region 212.

Figure 6:
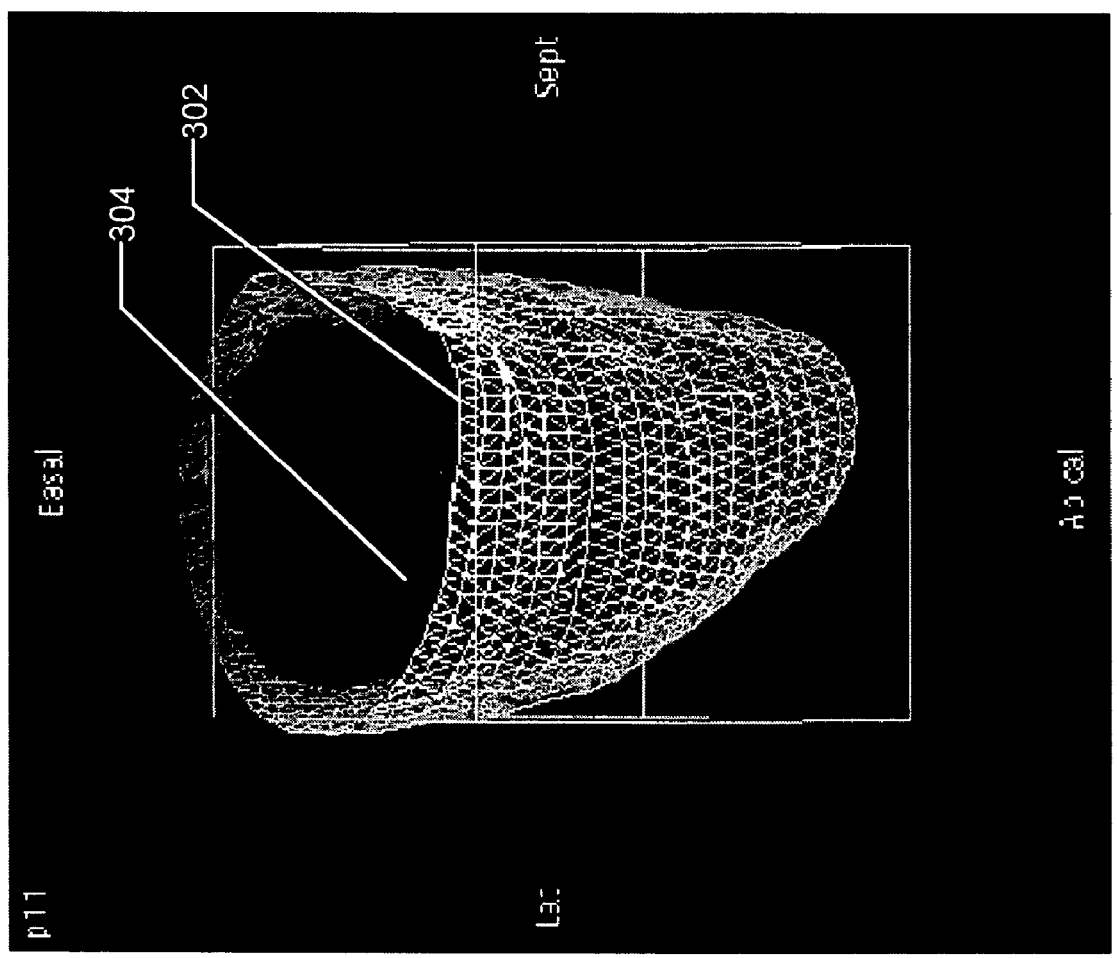
FIG. 6 is an example of a pre-systole cardiac CT image in wire mesh format showing the epicardium (outer wall) and endocardium (inner wall) of the left ventricle.
Figure 7:
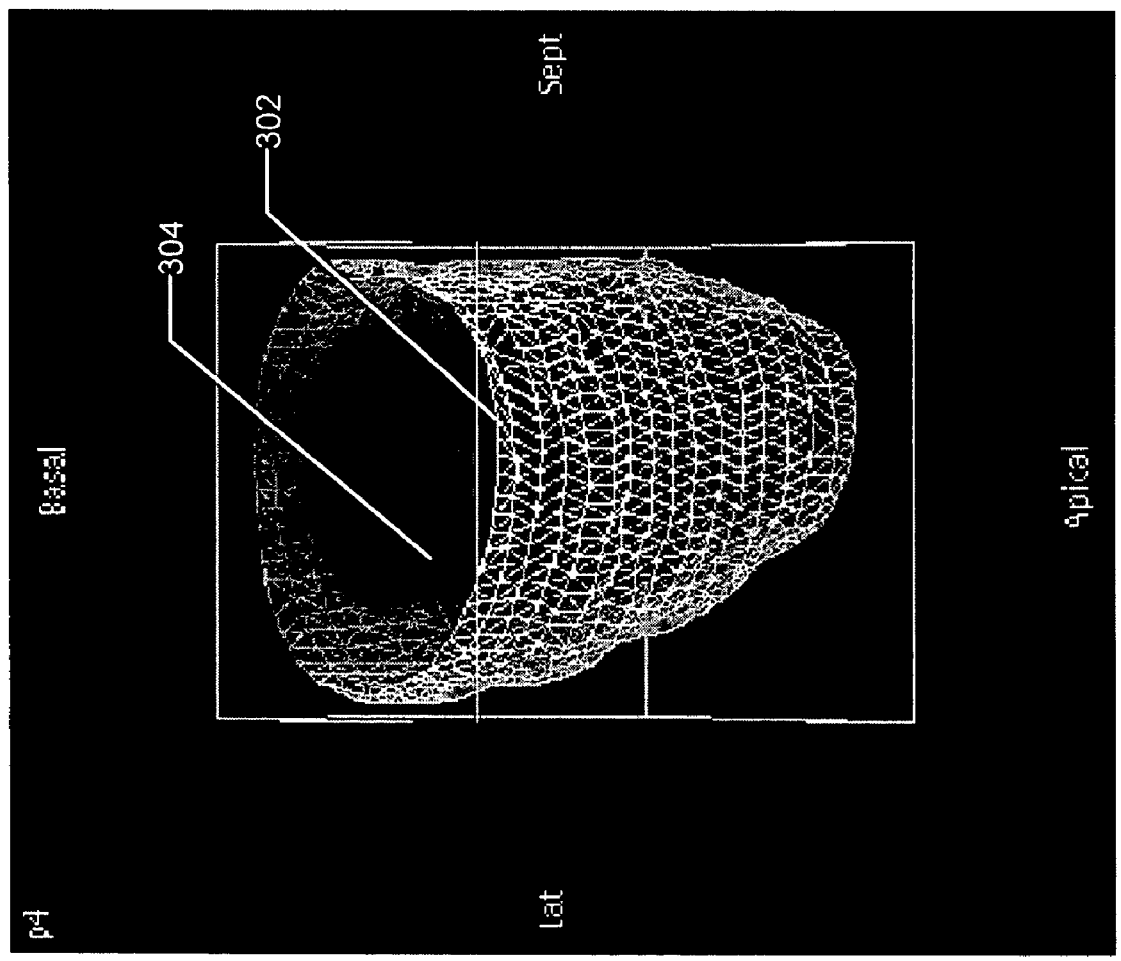
FIG. 7 is an example of an end systole cardiac CT image in wire mesh format showing the epicardium (outer wall) and endocardium (inner wall) of the left ventricle.

The LV wall motion profiles of the heart are used at 112 to detect the wall motion of each short axis slice between phases of the heart cycle with respect to a reference phase. Displacement and velocity profiles of the LV for each segment and/or slice are then created at 114 to localize at least one of the region indicating time delays of contraction, the region most recently attaining maximum displacement, or the region that most recently started contraction (i.e., the most recent region to attain maximum velocity). Wire mesh models are generated in some configurations to detect these regions. For example, FIG. 6 shows a cardiac CT image in wire mesh format showing the outer wall of the heart (the epicedium 302) and inner wall (the endocardium 304) at presystole. FIG. 7 is an image of the same heart at the end systole position of the cardiac cycle.

Next, 2D and/or 3D renderings of the LV are generated at 116. The renderings are overlaid with color-coded maps of the time delays of contraction, and/or the corresponding maximum displacement/velocity.

Major vessels are visualized at 118, including the CS and its branches, coronary arteries and their branches and fat on a translucent 3D model of the heart to avoid placement of leads onto regions proximal to major vessels. Necrotic tissues are visualized on the 3D model of the LV at 120 to avoid placement of leads onto regions that are ineffective. Explicit geometric markers are inserted into the volume at landmarks of interest and the thoracic wall at 122. In some configurations, LV and CS are visualized in a translucent fashion with the opaque geometric landmarks.

Specific 3D renderings and axial images (as DICOM images, video clips, films, multimedia formats, etc.) are saved at 124 as desired for visual reference for the interventional planning. Saved views can be exported and registered with a projection image on a fluoroscopy system or tomosysnthesis images of a 3D fluoroscopy system, or a computer workstation of an interventional system.

The most suitable site for placement of the pacing electrode on the LV wall is identified and displayed at 126, as are the next best region(s) for placement of this electrode in some configurations. If a transvenous approach using the CS is used, the CS branch closest to the optimal (or at least an advantageous site) is identified at 126.

The distance from the thoracic wall to the appropriate site(s) on the LV is identified and relevant dimensions are estimated and displayed at 128 to aid in choosing the appropriate pacing lead site. The distance that the lead has to travel in the CS before turning down into a branch is also estimated and displayed at 130. In some configurations, the branch used for that estimate is a branch determined to be optimal for pacing.

In some configurations, automatic methods are employed to perform any of the above functions using one or more of several computer-assisted detection and visualization methods, such as quantitative analysis of perfusion defects, localized contractility profile (LV wall movement), and/or identification of blood vessels using the continuity of same intensity levels. These methods can be run automatically when the procedure and the organ of interest is specified or can be run at least partly interactively with input from a user.

Configurations of the present invention disclosed above are implemented as part of a computed tomographic (CT) imaging system 10, wherein image reconstructor 34 (which may be part of computer 36) performs high-speed image reconstruction and performs other calculations and determinations under software or formware control. Images are visualized on display 42, and computer 36 and image reconstructor 34 include internal random access memory (RAM) and/or other memory storage, such as ROM, optical disk storage, magnetic disk storage, flash ROM, etc. The various types of memory and the general use of memory in computer systems for storing and retrieving data and intermediate results is known in the art.

In some configurations, the processes described herein (other than obtaining an image dataset) is performed using an already-obtained image dataset. Such configurations can utilize computer 36, display 42 and memory associated with computer 36 to perform one or more of the method configurations described herein, or a stand-alone workstation configured with appropriate software and/or formware. In some configurations, one or more machine readable media 52 are provided on which are recorded instructions that are configured to instruct a processor to perform steps of one or more of the method configurations described herein. As used herein, a "machine readable medium having instructions recorded thereon" is not to be construed as limited to a single type of medium or a single instance of a medium. Thus, a "machine readable medium" should be construed as including configurations comprising more than one media or media type. For example, a set of instructions comprising a computer program may be so long as to require multiple floppy diskettes or CD-ROMs, or a combination of the two. The combination of media on which the computer program instructions is recorded is considered as a "machine readable medium" as that term is used herein.

It will be appreciated that some configurations of the present invention aid in navigating pacing leads in real time to a location that achieves the most coordinated ventricular contraction. Some configurations provide similar assistance that can be used in other than real time for planning purposes. Also, some configurations of the present invention can play a significant role in providing LV anatomy and function and thus identify the most appropriate location for lead placement, thereby providing reduced overall procedure time and increased efficacy and safety.

In particular, in some configurations, a road map created to identify an optimal site for pacing is created, allowing a location and position of a CS branch that is closest to an optimal site to be identified. Also, the identification of an optimal site for lead placement provided by some configurations of the present invention improves the efficacy of techniques used for biventricular pacing, irrespective of the technique used (e.g., either placement of an LV lead into one of the CS branches or from an epicardial approach). Furthermore, the creation of a roadmap prior to identifying the best technique to use simplifies the procedure and improves safety in addition to improving efficacy.

While the invention has been described in terms of various specific embodiments, those skilled in the art will recognize that the invention can be practiced with modification within the spirit and scope of the claims.

What is claimed is:

1. A method for assisting the planning of an interventional biventricular pacing procedure, said method comprising:
    acquiring a volume of data of a heart of a patient in diastolic phase and in a plurality of phases of systole and early diastole, said acquired volume of data thereby becoming an image dataset, the heart having a left ventricle (LV), LV myocardium, a myocardial wall, an LV wall, and a cardiac cycle having a plurality of phases;
    extracting a surface of the left ventricle (LV) and the LV myocardium by segmenting the image dataset;
    dividing the LV into myocardial segments or into a plurality of short axis slices using the segmented image dataset;
    detecting wall motion of each myocardial segment or short axis slice between phases of the cardiac cycle with respect to a reference phase;
    generating a plurality of maps based on the detected wall motion for each myocardial segment or short axis slice at each of the phases of the cardiac cycle;
    localizing a region of the LV represented by the generated map most recently attaining maximum displacement and a region most recently attaining maximum velocity;
    generating a plurality of 2D or 3D renderings including renderings indicating at least one of time delays of contraction, a maximum displacement and a maximum velocity;
    overlaying onto a first map a first generated rendering indicating at least one of time delays of contraction, a maximum displacement and a maximum velocity; and
    overlaying onto a second map a second generated rendering indicating at least one of time delays of contraction, a maximum displacement and a maximum velocity that is not indicated in the first generated rendering.

2. A method in accordance with claim 1 wherein the patient has a thoracic wall, and the heart has LV walls, LV blood vessels including a coronary sinus (CS), and epicardial fat, said segmenting the image dataset is performed under control of post-processing software, and said generating 3D renderings further comprises visualizing the thoracic wall, LV walls, LV blood vessels, and epicardial fat using at least one of 3D surface rendering or volume rendering.

3. A method in accordance with claim 1 further comprising utilizing a visualization of a perfusion study to identify necrosed tissue of the LV myocardium and said generating 3D renderings further comprises visualizing the identified necrosed tissue.

4. A method in accordance with claim 3 further comprising determining anatomical location of necrosed tissue.

5. A method in accordance with claim 1 wherein said utilizing the segmented image dataset to divide the LV into a plurality of short axis slices or myocardial segments comprises dividing the LV into a basal segment, a said segment, and an apical segment.

6. A method in accordance with claim 1 wherein the heart further comprises a cardiac sinus (CS) having branches and coronary arteries having branches, and fat, and said generating 3D renderings further comprises visualizing the CS and its branches, coronary arteries and their branches, and fat on a translucent 3D model of the heart to facilitate placement of leads onto regions proximate major vessels.

7. A method in accordance with claim 1 further comprising identifying necrosed tissue of the LV myocardium and further wherein said generating 3D renderings further comprises visualizing the identified necrotic tissue on a 3D model of the LV to facilitate avoiding placement of leads onto ineffective regions.

8. A method in accordance with claim 1 wherein said generating 3D renderings further comprises inserting geometric markers into a visualized volume at landmarks of interest.

9. A method in accordance with claim 8 wherein said generating 3D renderings further comprises visualizing the LV in a translucent fashion and said geometric markers in an opaque fashion.

10. A method in accordance with claim 1 further comprising determining and visualizing a suitable site for at least one of placement of an epicardial pacing electrode on the LV wall or of placement of an endocardial pacing electrode in a suitable branch of a coronary sinus (CS) of the patient closest to an optimal pacing site.

11. A method in accordance with claim 10 wherein the patient has a thoracic wall, and further comprising determining and displaying a distance from the thoracic wall to the suitable site on the LV wall.

12. A method in accordance with claim 11 wherein the heart has a cardiac sinus (CS), and further comprising estimating and displaying a distance that a lead of the endocardial pacing electrode must travel in the CS before turning a branch.

13. A system for assisting the planning of an interventional biventricular pacing procedure for a heart of a patient having a left ventricle (LV), LV myocardium, a myocardial wall, an LV wall, and a cardiac cycle having a plurality of phases, said system comprising a processor and an imaging apparatus configured to acquire a volume of data of a heart of a patient in diastolic phase and in a plurality of phases of systole and early diastole, said acquired volume of data thereby becoming an image dataset and said processor configured to:
 extract a surface of the left ventricle (LV) and the LV myocardium by segmenting the image dataset;
 divide the LV into myocardial segments or into a plurality of short axis slices using the segmented image dataset;
 detect wall motion of each myocardial segment or short axis slice between phases of the cardiac cycle with respect to a reference phase;
 generate a map based on the detected wall motion for each myocardial segment or short axis slice at each of the phases of the cardiac cycle;
 localize at least one of a region of the LV represented by the generated map indicating time delays of contraction, a region of the LV represented by the generated map most recently attaining maximum displacement, or a region of the LV represented by the generated map most recently attaining maximum velocity; and
 generate 2D or 3D renderings including renderings indicating at least two of time delays of contraction, a maximum displacement, and a maximum velocity.

14. A system in accordance with claim 13 wherein the patient has a thoracic wall, and the heart has LV walls, LV blood vessels, and epicardial fat, and wherein said system is configured to segment the image dataset under control of post-processing software, and to generate said 3D renderings, said system is further configured to visualize the thoracic wall, LV walls, LV blood vessels, and epicardial fat using at least one of 3D surface rendering or volume rendering.

15. A system in accordance with claim 13 further configured to utilize a visualization of a perfusion study to identify necrosed tissue of the LV myocardium and wherein to generate said 3D renderings, said apparatus is further configured to visualize the identified necrosed tissue.

16. A system in accordance with claim 13 wherein to utilize said segmented image dataset to divide the LV into a plurality of short axis slices or segmented myocardial regions, said system is configured to divide the LV into a basal segment, a said segment, and an apical segment.

17. A system in accordance with claim 13 wherein the heart further comprises a cardiac sinus (CS) having branches and coronary arteries having branches, and fat, and to generate said 3D renderings, said system is further configured to visualize the CS and its branches, coronary arteries and their branches, and fat on a translucent 3D model of the heart to facilitate placement of leads onto regions distal from major vessels.

18. A system in accordance with claim 13 further configured to identify necrosed tissue of the LV myocardium and wherein to generate said 3D renderings, said system is further configured to visualize the identified necrotic tissue on a 3D model of the LV to facilitate avoiding placement of leads onto ineffective regions.

19. A system in accordance with claim 13 wherein to generate said 3D renderings, said system is further configured to insert geometric markers into a visualized volume at landmarks of interest.

20. A system in accordance with claim 19 wherein to generate said 3D renderings, said system is further configured to visualize the LV in a translucent fashion and said geometric markers in an opaque fashion.

21. A system in accordance with claim 13 further configured to determine and visualize a suitable site for at least one of placement of an epicardial pacing electrode on the LV wall or of placement of an LV pacing lead into a branch of a coronary sinus (CS) of the patient.

22. A system in accordance with claim 21 wherein the patient has a thoracic wall, and said system is further configured to determine and display a distance from the thoracic wall to the suitable site on the LV wall.

23. A system in accordance with claim 22 wherein the heart has a cardiac sinus (CS), and said system is further configured to estimate and display a distance that an LV pacing lead must travel in the CS before turning down a branch suitable for pacing.

24. A method for assisting the planning of an interventional biventricular pacing procedure, said method comprising:
 extracting a surface of a left ventricle (LV) and a LV myocardium of the patient's heart by segmenting an image dataset of a heart of a patient;
 dividing the LV into myocardial segments or into a plurality of short axis slices using the segmented image dataset;

detecting wall motion of each myocardial segment or short axis slice of phases of a cardiac cycle of the patient's heart with respect to a reference phase;

generating a map based on the detected wall motion for each myocardial segment or short axis slice at each of the phases of the cardiac cycle;

localizing a region of the LV represented by the generated map most recently attaining maximum displacement and a region most recently attaining maximum velocity; and generating 2D or 3D renderings including renderings indicating at least two of time delays of contraction, a maximum displacement, and a maximum velocity.

25. A method in accordance with claim 24 wherein the patient has a thoracic wall, and the heart has LV walls, LV blood vessels, and epicardial fat, said segmenting the image dataset is performed under control of post-processing software, and said generating 3D renderings further comprises visualizing the thoracic wall, LV walls, LV blood vessels, and epicardial fat using at least one of 3D surface rendering or volume rendering.

26. A method in accordance with claim 25 further comprising providing measurements indicating distances from skin to heart wall.

27. A method in accordance with claim 24 further comprising utilizing a visualization of a perfusion study to identify necrosed tissue of the LV myocardium and said generating 3D renderings further comprises visualizing the identified necrosed tissue.

28. A method in accordance with claim 24 wherein said utilizing the segmented image dataset to divide the LV into myocardial segments or into a plurality of short axis slices comprises dividing the LV into a basal segment, a said segment, and an apical segment.

29. A method in accordance with claim 24 wherein the heart further comprises a cardiac sinus (CS) having branches and coronary arteries having branches, and fat, and said generating 3D renderings further comprises visualizing the CS and its branches, coronary arteries and their branches, and fat on a translucent 3D model of the heart to facilitate placement of leads onto regions proximate major vessels, 30. A method in accordance with claim 24 further comprising identifying necrosed tissue of the LV myocardium and further wherein said generating 3D renderings further comprises visualizing the identified necrotic tissue on a 3D model of the LV to facilitate avoiding placement of leads onto ineffective regions.

31. A method in accordance with claim 30 wherein said generating 3D renderings further comprises inserting geometric markers into a visualized volume at landmarks of interest.

32. A method in accordance with claim 30 further comprising determining and visualizing a suitable site for at least one of placement of an epicardial pacing electrode a pacing electrode on the LV wall or of placement of an endocardial pacing electrode in a branch of a coronary sinus (CS) of the patient.

33. A method in accordance with claim 32 wherein the patient has a thoracic wall, and further comprising determining and displaying a distance from the thoracic wall to the suitable site on the LV wall.

34. A method in accordance with claim 33 wherein the heart has a cardiac sinus (CS), and further comprising estimating and displaying a distance that a lead of the endocardial pacing electrode must travel in the CS before turning down a branch.

35. A computer readable medium having recorded thereon instructions configured to instruct a processor to:

extract a surface of a left ventricle (LV) and a LV myocardium of the patient's heart by segmenting an image dataset of a heart of a patient;

divide the LV into myocardial segments or into a plurality of short axis slices utilizing the segmented image dataset;

detect wall motion of each myocardial segment or short axis slice between phases of a cardiac cycle with respect to a reference phase;

generate a map based on the detected wall motion for each myocardial segment or short axis slice at each of the phases of the cardiac cycle;

localize a region of the LV represented by the generated map most recently attaining maximum displacement and a region most recently attaining maximum velocity; and generate 2D or 3D renderings including renderings indicating at least two of time delays of contraction, a maximum displacement, and a maximum velocity.

36. A computer readable medium in accordance with claim 35 wherein said instructions are further configured to instruct the processor to visualize a thoracic wall, LV walls, LV blood vessels, and epicardial fat of the patient using at least one of 3D surface rendering or volume rendering.

37. A computer readable medium in accordance with claim 35 wherein to utilize the segmented image dataset to divide the LV into myocardial segments or into a plurality of short axis slices, said instructions are configured to instruct the processor to divide the LV into a basal segment, a said segment, and an apical segment.

38. A computer readable medium in accordance with claim 35 wherein to generate 3D renderings, said instructions are further configured to instruct the processor to visualize the patient's cardiac sinus and its branches, coronary arteries and their branches, and fat on a translucent 3D model of the heart to facilitate placement of leads onto regions proximate major vessels.

39. A computer readable medium in accordance with claim 35 wherein said instructions are further configured to instruct the processor to identify necrosed tissue of the LV myocardium and further wherein to generate 3D renderings, said instructions are further configured to instruct the processor to visualize the identified necrotic tissue on a 3D model of the LV to facilitate avoiding placement of leads onto ineffective regions.

40. A computer readable medium in accordance with claim 35 wherein to generate 3D renderings, said instructions are further configured to instruct the processor to insert geometric markers into a visualized volume at landmarks of interest.

41. A computer readable medium in accordance with claim 35 wherein said instructions are further configured to instruct the processor to determine and visualize a suitable site for placement of an epicardial pacing electrode on the LV wall.

42. A computer readable medium in accordance with claim 41 wherein said instructions are further configured to determine and display a distance from the thoracic wall to the suitable site on the LV wall.

43. A computer readable medium in accordance with claim 41 wherein said instructions are further configured to estimate and display a distance that a lead of an endocardial pacing electrode must travel in a cardiac sinus of the patient's heart before turning down a branch.

44. A computer system for assisting the planning of an interventional biventricular pacing procedure for a heart of a patient having a left ventricle (LV), LV myocardium, a myocardial wall, an LV wall, and a cardiac cycle having a plurality of phases, said computer system having a processor, memory, and a display, and said processor configured to:

extract a surface of the left ventricle (LV) and the LV myocardium of the patient's heart by segmenting an image dataset of the heart of the patient;

divide the LV into myocardial segments or into a plurality of short axis slices utilizing the segmented image dataset;

detect wall motion of each myocardial segment or short axis slice between phases of a cardiac cycle with respect to a reference phase;

generate a map based on the detected wall motion for each myocardial segment or short axis slice at each of the phases of the cardiac cycle;

localize at least one of a region of the LV represented by the generated map most recently attaining maximum displacement and a region most recently attaining maximum velocity; and generate 2D or 3D renderings including renderings indicating at least two of time delays of contraction, a maximum displacement, and a maximum velocity.

45. A computer system in accordance with claim 44 further configured to visualize a thoracic wall, LV walls, LV blood vessels, and epicardial fat of the patient using at least one of 3D surface rendering or volume rendering.

46. A computer system in accordance with claim 44 wherein to utilize the segmented image dataset to divide the LV into segments or into a plurality of short axis slices, said computer system is configured to divide the LV into a basal segment a said segment, and an apical segment.

47. A computer system in accordance with claim 44 wherein to generate 3D renderings, said computer system is further configured to visualize the patient's cardiac sinus and its branches, coronary arteries and their branches, and fat on a translucent 3D model of the heart to facilitate placement of leads onto regions proximate major vessels.

48. A computer system in accordance with claim 44 further configured to identify necrosed tissue of the LV myocardium and further wherein to generate 3D renderings, said computer system is configured to visualize the identified necrotic tissue on a 3D model of the LV to facilitate avoiding placement of leads onto ineffective regions.

49. A computer system in accordance with claim 44 wherein to generate 3D renderings, said computer system is further configured to insert geometric markers into a visualized volume at landmarks or interest.

50. A computer system in accordance with claim 44 further configured to determine and visualize a suitable site for placement of an epicardial pacing electrode on the LV wall.

51. A computer system in accordance with claim 50 further configured to determine and display a distance from the thoracic wall to the suitable site on the LV wall.

52. A computer system in accordance with claim 50 further configured to estimate and display a distance that a lead of an endocardial pacing electrode must travel in a cardiac sinus of the patient's heart before turning down a branch.

* * * * *

UNITED STATES PATENT AND TRADEMARK OFFICE
CERTIFICATE OF CORRECTION

PATENT NO. : 7,613,500 B2
APPLICATION NO. : 10/900847
DATED : November 3, 2009
INVENTOR(S) : Vass et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 891 days.

Signed and Sealed this

Nineteenth Day of October, 2010

David J. Kappos
*Director of the United States Patent and Trademark Office*